United States Patent [19]

Nomura et al.

[11] Patent Number: 5,697,376
[45] Date of Patent: Dec. 16, 1997

[54] PHYSICAL INFORMATION COLLECTION SYSTEM

[75] Inventors: Takashi Nomura, Komaki; Toshihiko Ogura, Inuyama, both of Japan

[73] Assignee: Colin Corporation, Aichi-ken, Japan

[21] Appl. No.: 325,580

[22] Filed: Oct. 19, 1994

[30] Foreign Application Priority Data

Nov. 29, 1993 [JP] Japan ................... 5-298384
Jan. 20, 1994 [JP] Japan ................... 6-000148 U

[51] Int. Cl.⁶ ................................................ A61B 5/00
[52] U.S. Cl. .................. 128/680; 128/681; 128/682; 128/633; 128/736; 128/672; 128/687; 128/630; 128/748; 128/691
[58] Field of Search .................... 128/670, 672, 128/677, 680–3, 687–691, 630, 633, 664–6, 736, 748, 632

[56] References Cited

U.S. PATENT DOCUMENTS

| | | | |
|---|---|---|---|
| 4,121,574 | 10/1978 | Lester | 128/666 |
| 4,767,917 | 8/1988 | Ushikubo | 235/381 |
| 4,854,329 | 8/1989 | Walruff | 128/745 |
| 5,193,541 | 3/1993 | Hatsuwi | 128/630 |
| 5,218,971 | 6/1993 | Minami et al. | 128/771 |
| 5,437,278 | 8/1995 | Wilk | 128/630 |

FOREIGN PATENT DOCUMENTS 5-137698  6/1993  Japan .

*Primary Examiner*—Robert L. Nasser
*Attorney, Agent, or Firm*—Oliff & Berridge

[57] ABSTRACT

A physical-information collecting system for collecting physical information of living subjects, including a registering device which registers sets of identification data each of which identifies a corresponding one of the living subjects; a card reading device into which a personal card having a set of identification data is inserted by a living subject, the card reading device reading the set of identification data from the personal card inserted therein; an identifying device which identifies whether the set of identification data read by the card reading device is same as one of the sets of identification data registered in the registering device; a measuring device which obtains physical information from the living subject who has inserted the personal card into the card reading device; a first memory device which stores, each time the measuring device obtains physical information from the living subject, the obtained physical information of the living subject, subject to a positive identification of the identifying device that the set of identification data read by the card reading device is same as one of the sets of identification data registered in the registering device; and an output device which outputs, subject to the positive identification of the identifying device, the physical information of the living subject accumulatively stored in the first memory device.

27 Claims, 14 Drawing Sheets

TO COMMUNICATION
INTERFACE 80

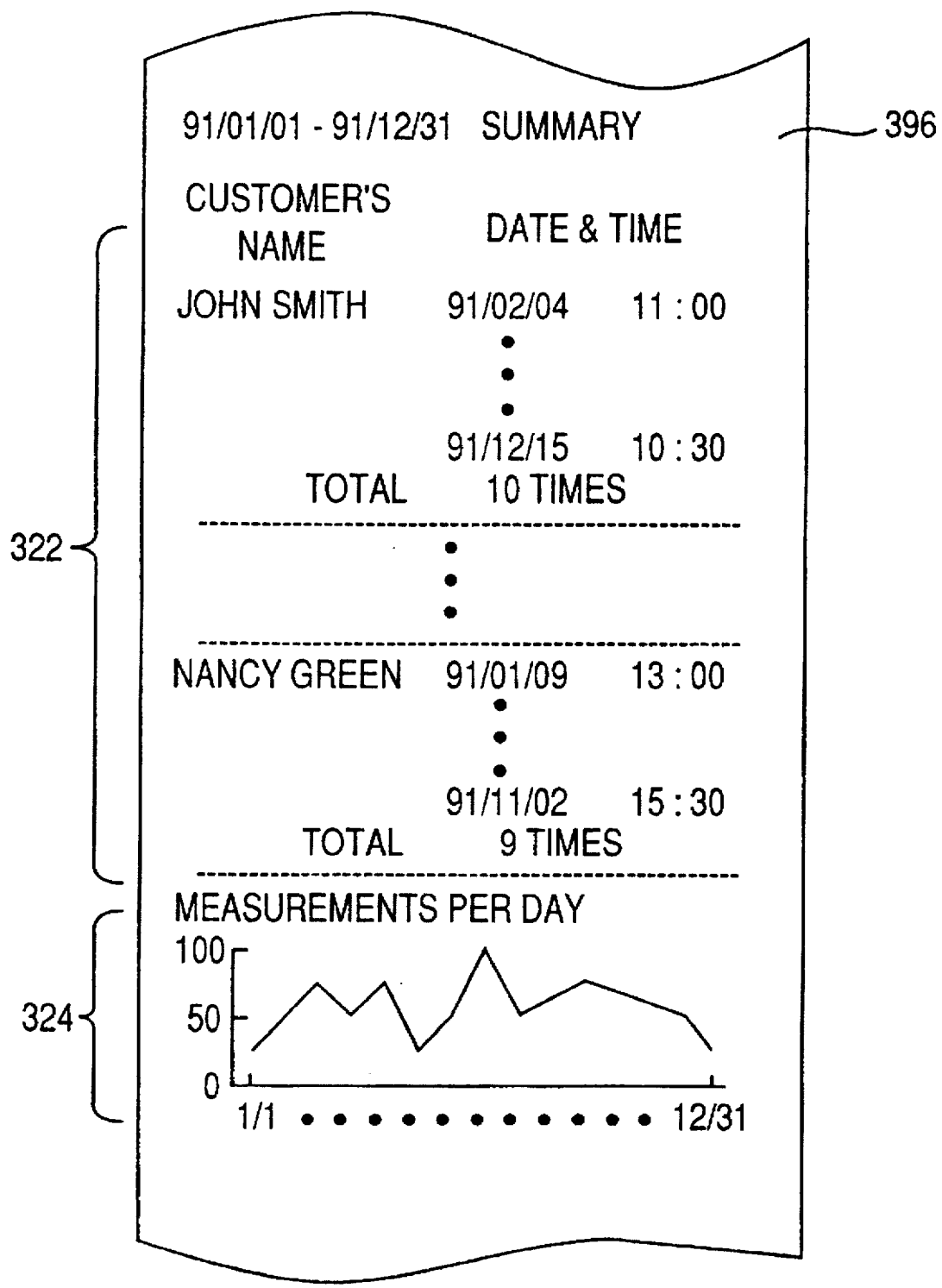

PHYSICAL INFORMATION COLLECTION SYSTEM

BACKGROUND OF THE INVENTION

1. Field of the Invention

The present invention relates to a physical information collecting system for collecting physical information (e.g., blood pressure) of living subjects.

2. Related Art Statement

There is known a physical-information collecting system which (a) measures one or more physical parameters such as blood pressure (BP), pulse rate (PR), respiration rate, blood oxygen saturation, and expired gas concentration, from a living subject, and (b) stores the obtained physical information in a personal card being carried by the person. An example of this collecting system is an automatic BP measuring apparatus disclosed in Japanese Patent Application laid open for inspection purpose under Publication No. 5-137698 on Jun. 1, 1993. The prior BP measuring apparatus is operated by a user, i.e., first inserting his personal card into a card read/write device of the apparatus, subsequently putting his or her arm into an arm receiver of the same, and then pressing a start switch of the same. The prior apparatus automatically measures blood pressure (BP) of the user and stores data indicative of the measured BP values in the personal card inserted in the card read/write device. The BP data stored in the personal card can be utilized for health care of the user. The prior BP measuring apparatus is disposed in not only a hospital but also various facilities such as a bank's office, post office, life insurance company, securities company, or athletic gym or club so that the apparatus may be used by their customers as one of their services to them.

Since the capacity of data storage of a personal card is considerably small, it is desirable to accumulatively store, each time physical information is obtained from a living subject by a physical-information obtaining apparatus (e.g., BP measuring apparatus), the obtained physical information in association with identification (ID) data of the person, in a data-storage device provided in the physical-information obtaining apparatus. This apparatus ensures that the accumulatively stored physical information of an identical person is easily read and outputted by inputting the ID data of the person, at the time of each physical-information obtaining operation or at any desired time. The accumulative physical information outputted from the apparatus includes the physical information obtained by the current physical-information obtaining operation.

In the above apparatus, however, the stored physical information of a certain person may possibly be outputted by a second person, e.g., intentionally or unintentionally inputting the correct ID data of the first person. In this case, the privacy of the first person may be violated by the second person. This is banned by the Drugs, Cosmetics and Medical Instruments Act of Japan.

Meanwhile, in the case where the stored physical information of a customer is outputted from the prior BP measuring apparatus disposed in a facility (e.g., bank's office) other than a hospital, it is desirable to output, in addition to the stored physical information of the customer, a piece of non-physical information for the purpose of differentiating its services from those of other facilities. The non-physical information may be "mini" information such as short and useful knowledge, proverb, motto, slogan, or short verse. In this case, in order to improve the differentiation of services, it is preferable to frequently change the piece of non-physical information with new ones.

SUMMARY OF THE INVENTION

It is therefore a first object of the present invention to provide a physical-information collecting system capable of effectively preventing the stored physical information of a living subject from being outputted by a different person.

The first object may be achieved according to a first aspect of the present invention, which provides a physical-information collecting system for collecting physical information of a plurality of living subjects, comprising (a) an identification data registering device which registers a plurality of sets of identification data each of which identifies a corresponding one of the living subjects; (b) a card reading device into which a personal card having a set of identification data is inserted by a living subject, the card reading device reading the set of identification data from the personal card inserted therein; (c) identification data identifying means for identifying whether the set of identification data read by the card reading device is same as one of the sets of identification data registered in the identification data registering device; (d) a measuring device which obtains physical information from the living subject who has inserted the personal card into the card reading device; (e) a first memory device which stores, each time the measuring device obtains physical information from the living subject, the obtained physical information of the living subject, subject to a positive identification of the identification data identifying means that the set of identification data read by the card reading device is same as one of the sets of identification data registered in the identification data registering device; and an output device which outputs, subject to the positive identification of the identification data identifying means, the physical information of the living subject accumulatively stored in the first memory device.

In the physical-information collecting system constructed as described above, the first memory device accumulatively stores, each time the measuring device obtains physical information from the living subject, the obtained physical information of the living subject, subject to a positive identification of the identification data identifying means that the set of identification data read by the card reading device is same as one of the sets of identification data registered in the identification data registering device. The output device outputs, subject to the positive identification of the identification data identifying means, the physical information of the living subject accumulatively stored in the first memory device. Therefore, unless the set of identification data read by the card reading device coincides with any one of the sets of identification data registered in the identification data registering device, the physical information of a "registered" person stored in the first memory cannot be outputted. Thus, the present system effectively prevents the stored physical information of the registered person from being outputted by a second person who does not have the "registered" card of the first person.

According to a preferred feature of the first aspect of the present invention, the identification data registering device comprises a register mode select device which is operable for establishing a register mode in which, when the card reading device reads a plurality of sets of identification data from a plurality of personal cards including a registered personal card whose identification data is registered in the identification data registering device, the identification data registering device registers the sets of identification data read by the card reading device such that each of the thus registered sets of identification data identifies an identical person identified by the identification data of the registered personal card, the identification data identifying means providing the positive identification when the set of identification data read by the card reading device from the personal card of the living subject is same as one of a plurality of sets of identification data registered in the identification data registering device each of which identifies the living subject.

According to another feature of the first aspect of the present invention, the collecting system further comprises a second memory device which stores a plurality of sets of evaluation comment data each of which represents a corresponding one of a plurality of physical-information evaluation comments; selecting means for selecting at least one of the evaluation comments which corresponds to at least one of (a) the physical information of the living subject accumulatively stored in the first memory device and (b) the physical information of the living subject currently obtained by the measuring device; and the output device outputting the accumulatively stored physical information of the living subject, together with the at least one evaluation comment selected by the selecting means.

According to yet another feature of the first aspect of the present invention, the collecting system further comprises a second memory device which stores, each time non-physical information related to each of the living subjects whose identification data are registered in the identification data registering device is produced in the collecting system, the related non-physical information of the each living subject, in association with the registered identification data identifying the each living subject, the output device outputting the physical information of the each living subject accumulatively stored in the first memory device, together with the related non-physical information of the each living subject accumulatively stored in the second memory device.

According to a further feature of the first aspect of the present invention, the output device comprises at least one of (a) a printer which records, on a recording sheet, the physical information of the living subject accumulatively stored in the first memory device and (b) a display which displays the accumulatively stored physical information of the living subject.

According to another feature of the first aspect of the present invention, the measuring device measures at least one of a blood pressure and a pulse rate of the living subject.

According to another feature of the first aspect of the present invention, the collecting system further comprises a second memory device which stores, each time the measuring device obtains physical information from each of the living subjects whose identification data are stored in the identification data registering device, operation data related to operation of the collecting system when the first memory device stores the obtained physical information of the each living subject. In this case, the second memory device may store, as the operation data related to the operation of the collecting system, at least one of a date and a time when the first memory device stores the obtained physical information of the each living subject. The collecting system may further comprise a special data registering device which registers at least one set of special data identifying at least one special card different from the personal card of the living subject; the card reading device reading, when one of the at least one special card is inserted thereinto, the set of special data recorded on the one special card inserted therein; special data identifying means for identifying whether a set of data read by the card reading device is same as one of the at least one set of special data registered in the special data registering device; and an operation data output device which outputs the operation data accumulatively stored in the second memory device, subject to a positive identification of the special data identifying means that the set of data read by the card reading device is same as one of the at least one set of special data registered in the special data registering device.

It is a second object of the present invention to provide a physical-information collecting system capable of outputting the stored physical information of a living subject together with one of a plurality of pieces of non-physical information which are changeable with each other.

The second object may be achieved according to a second aspect of the present invention, which provides a physical-information collecting system for collecting physical information of a plurality of living subjects, comprising: (a) an identification data registering device which registers a plurality of sets of identification data each of which identifies a corresponding one of the living subjects; (b) a measuring device which obtains physical information from each of the living subjects; (c) a first memory device which stores, each time the measuring device obtains physical information from the each living subject, the obtained physical information of the each living subject in association with a corresponding one of the sets of identification data registered in the identification data registering device; (d) a card reading device into which one of a plurality of information cards each of which has a plurality of pieces of non-physical information is inserted, the card reading device reading the piece of non-physical information recorded on the one information card inserted therein; (e) a second memory device which stores the non-physical information read by the information reading device; and (f) an output device which outputs the physical information of the each living subject accumulatively stored in the first memory device, together with the non-physical information stored in the second memory device.

In the physical-information collecting system constructed as described above, the output device outputs the physical information of the each living subject accumulatively stored in the first memory device, together with the non-physical information stored in the second memory device. The card reading device reads, when one of a plurality of information cards each of which has a corresponding one of a plurality of pieces of non-physical information is inserted thereinto, the piece of non-physical information recorded on the one information card inserted therein, and the second memory device stores the non-physical information read by the information reading device. Therefore, the plurality of pieces of non-physical information are easily changeable so as to be outputted with the stored physical information of each living subject. A piece of non-physical information recorded on an information card may be a set of image data representing a predetermined image which may comprise a plurality of characters constituting a meaningful sentence, paragraph, or passage.

According to a preferred feature of the second aspect of the present invention, the collecting system further comprises a special data registering device which registers at least one set of special data identifying at least one special card different from the information cards; the card reading device reading, when one of the at least one special card is inserted thereinto, the set of special data recorded on the one special card inserted therein; special data identifying means for identifying whether a set of data read by the card reading device is same as one of the at least one set of special data registered in the special data registering device; a third memory device which stores, each time the measuring device obtains physical information from the each living subject, operation data related to operation of the collecting system when the first memory device stores the obtained physical information of the each living subject; and an operation data output device which outputs the operation data accumulatively stored in the third memory device, subject to a positive identification of the special data identifying means that the set of data read by the card reading device is same as one of the at least one set of special data registered in the special data registering device. In this case, the operation data of the collecting system is easily outputted and utilized. The third memory device may store, as the operation data related to the operation of the collecting system, at least one of a date and a time when the first memory device stores the obtained physical information of the each living subject.

The second object may also be achieved according to a third aspect of the present invention, which provides a physical-information collecting system for collecting physical information of a plurality of living subjects, comprising: (a) an identification data registering device which registers a plurality of sets of identification data each of which identifies a corresponding one of the living subjects; (b) a measuring device which obtains physical information from each of the living subjects; (c) a first memory device which stores, each time the measuring device obtains physical information from the each living subject, the obtained physical information of the each living subject in association with a corresponding one of the sets of identification data registered in the identification data registering device; (d) selecting means for selecting one of a plurality of pieces of non-physical information recorded on a recording medium; (e) information reading means which reads the one piece of non-physical information selected by the selecting means; (f) a second memory device which stores the non-physical information read by the information reading means; and (g) an output device which outputs the physical information of the each living subject accumulatively stored in the first memory device, together with the non-physical information stored in the second memory device.

In the physical-information collecting system constructed as described above, the output device outputs the physical information of the each living subject accumulatively stored in the first memory device, together with one piece of non-physical information stored in the second memory device. The selecting means selecting one of a plurality of pieces of non-physical information recorded on a recording medium, the information reading means reads the non-physical information selected by the selecting means, and the second memory device stores the non-physical information read by the information reading means. Thus, the plurality of pieces of non-physical information are easily changeable so as to be outputted with the stored physical information of each living subject. Each of the pieces of non-physical information recorded on a recording medium may be a set of image data representing a predetermined image.

According to a preferred feature of the third aspect of the present invention, the information reading means comprises a card reading device which reads, from an information card as the recording medium, the one piece of non-physical information recorded on the information card.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 13 is a view of a record sheet as an output of the collecting system operated according to the main routine of FIG. 6.

DETAILED DESCRIPTION OF THE PREFERRED EMBODIMENTS

Figure 1:
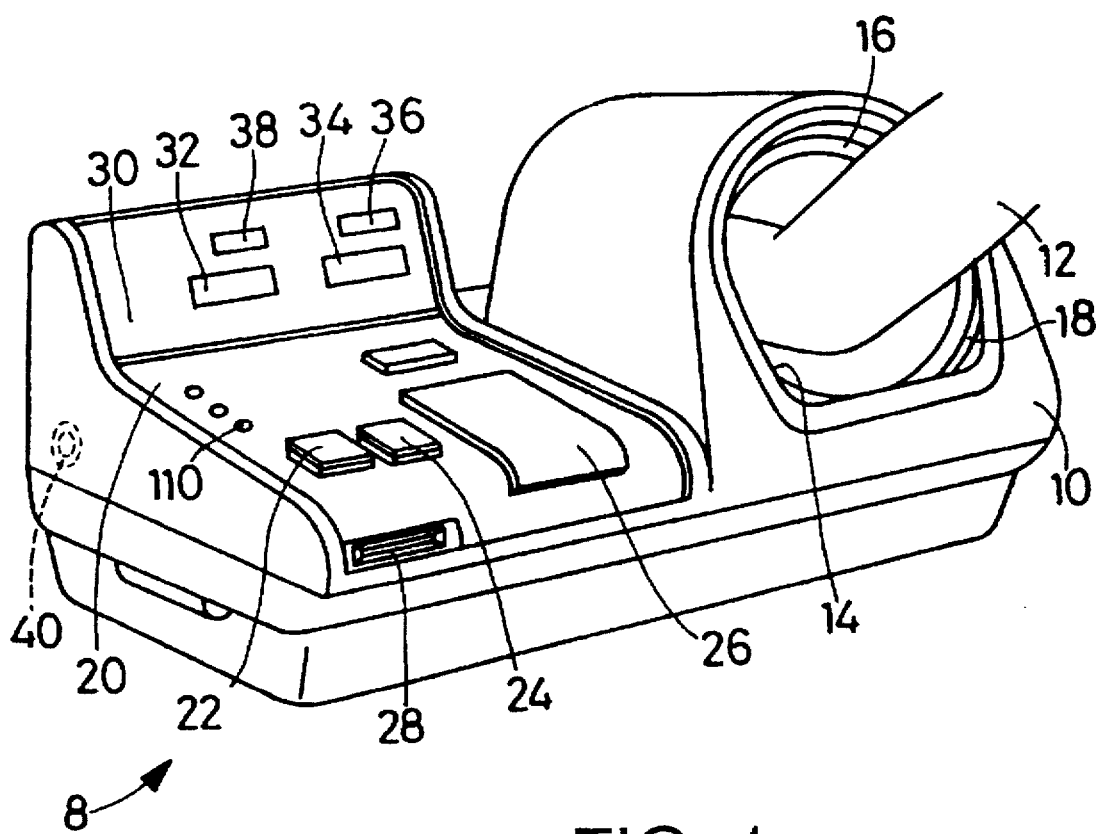
FIG. 1 is a perspective view of an automatic blood pressure (BP) measuring apparatus as a part of a physical-information collecting system in accordance with the present invention.

Referring first to FIG. 1, there is shown an automatic blood pressure (BP) measuring apparatus 8 as a part of a physical-information collecting system to which the present invention is applied. In the figure, reference numeral 10 designates a housing of the BP measuring apparatus 8. The apparatus 8 includes a generally cylindrical hollow section which serves as an arm receiver 14 into which a living subject 12 inserts his or her arm for measuring blood pressure and pulse rate. The present collecting system is disposed in, e.g., a bank's office for being used by its customers while they are waiting for their turns.

Inside the arm receiver 14, an elongate belt 18 (FIG. 2) takes a generally cylindrical shape. To the inner surface of the elongate belt 18, is secured an inflatable cuff 16 constituted by a bag-like flexible cloth and a rubber bag enveloped inside the flexible cloth. The BP measuring apparatus 8 has an operation panel 20 including a START switch 22, a STOP switch 24, a printer 26, and a card insertion slot 28. The apparatus 8 also has a display panel 30 including a SYS display 32, a DIA display 34, a PR display 36, and a day-of-time display 38. The abbreviations 'SYS', 'DIA' and 'PR' represent a systolic and a diastolic blood pressure and a pulse rate, respectively. The apparatus 8 also includes a speaker 40 in the side wall thereof. The speaker 40 issues various sound messages to the user.

Figure 2:
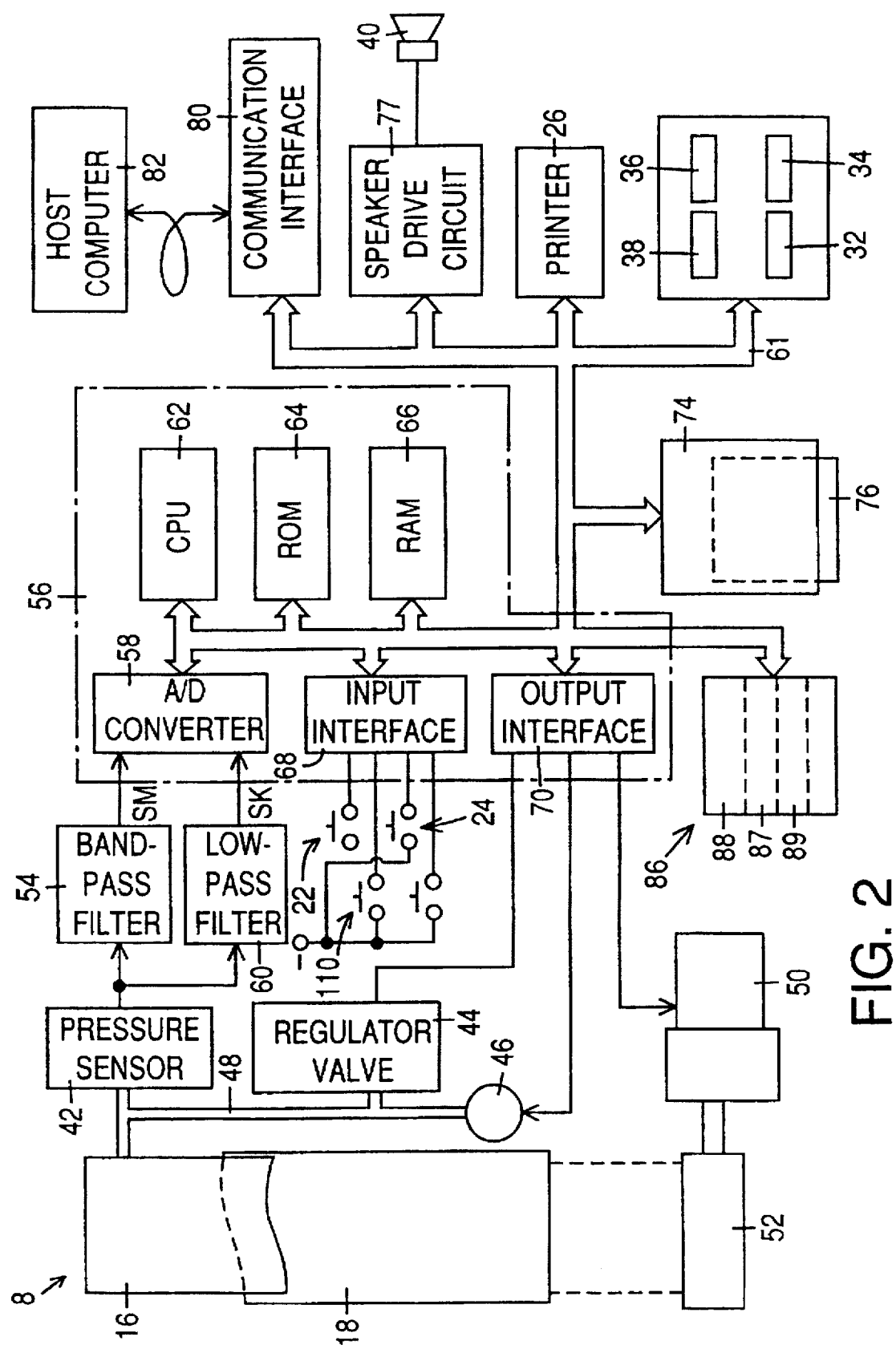
FIG. 2 is a diagrammatic view of the electric construction of the collecting system.

FIG. 2 shows the electric construction of the present collecting system including the BP measuring apparatus 8. As shown in this figure, the inflatable cuff 16 is connected via piping 48 to a pressure sensor 42, a cuff pressure regulator valve 44, and an air pump 46. The elongate belt 18, which takes a cylindrical shape in the arm receiver 14 and to which the inflatable cuff 16 is secured, is fixed at one of opposite ends thereof to the housing 10 and is connected at the other end to a rotatable drum 52, which is driven or rotated by a direct current (DC) motor 50 associated with reduction gears. The elongate belt 18 or inflatable cuff 16 is tightened, and loosened, by the DC motor 50.

The output signal of the pressure sensor 42 is fed to a band-pass filter 54 which selectively transmits a heartbeat-synchronous oscillatory component of the received pressure signal, as a pulse wave signal, SM, to an analog to digital (A/D) converter 58 of an arithmetic and control circuit 56. The pulse wave signal SM represents the pressure pulse wave produced from the pressed arteries of the subject's arm 12 and propagated to the inflatable cuff 16 currently pressing the arm 12. The pressure signal of the pressure sensor 42 is also fed to a low-pass filter 60 which selectively transmits a static component of the received signal as a cuff pressure signal, SK, to the A/D converter 58 of the control circuit 56. The cuff pressure signal SK represents the static pressure in the inflatable cuff 16.

The arithmetic and control circuit 56 is essentially constituted by a microcomputer including a central processing unit (CPU) 62, a read only memory (ROM) 64, a random access memory (RAM) 66, an input interface circuit 68, an output interface circuit 70, and a data bus 61. The CPU 62 processes input signals according to the control programs pre-stored in the ROM 64 by utilizing the temporary-storage function of the RAM 66, and produces drive and display signals. For the blood pressure and pulse rate measurement, the CPU 62 feeds drive signals to the DC motor 50, subsequently to the air pump 46, and then to the cuff-pressure regulator valve 44, so that the CPU 62 receives the pulse wave signal SM and the cuff-pressure signal SK from the pressure sensor 42 via the respective filters 54, 60, determines based on the received signals SM, SK the BP and PR values of the living subject 12, feeds display signals to the SYS, DIA, and PR displays 32, 34, 36, and generates print signal to the printer 26.

The CPU 62 is connected to a storage device 86 which may include a magnetic disk, magnetic tape, or non-volatile semiconductor memory. The storage device 86 has an evaluation-comment memory area 87 in which are pre-stored a plurality of sets of evaluation-comment data each of which is indicative of a corresponding one of a plurality of predetermined BP and/or PR evaluation comments. The stored evaluation comments comprise, e.g., "HIGH BLOOD PRESSURE IS SUSPECTED" and "LOW BLOOD PRESSURE IS SUSPECTED". The CPU 62 selects, according to specific control programs pre-stored in the ROM 64, one or more stored evaluation comments which correspond to the BP and PR values of the subject 12 measuredly the apparatus 8 in the current operation, and/or the collected BP and PR values of the identical subject measured by the apparatus 8 and accumulatively stored in a physical-information memory area 88 of the storage device 86. The collected BP and PR values of the subject 12 contain the values obtained by the apparatus 8 in the current operation, in addition to the values obtained by the apparatus 8 in the past operations when the subject 12 had called at the bank's office. The CPU 62 may be adapted to feed sound signal to a speaker drive circuit 77 to drive the speaker 40 and thereby issue the selected one or more evaluation comments. The storage device 86 additionally includes an identification (ID) data memory area 89 for storing one or more sets of ID data each of which identifies a corresponding one of a plurality of bank's customers. Those customers are registered in the apparatus 8 by storing their ID data in the memory area 89. The CPU 62 is also connected to a card reader 74 for receiving a magnetic card 76 inserted through the insertion slot 28 by a customer and reading ID data recorded on the magnetic card 76. The ID data recorded on the magnetic card 76 serve as ID data identifying the customer carrying the card 76.

The BP measuring apparatus 8 is connected to a host computer 82 of the bank via a communication interface 80, so that the microcomputer 56 of the apparatus 8 can transmit and receive various kinds of information to and from the host computer 82. The host computer 82 has a memory device in which are stored information related to each of the customers who have their accounts with the bank. The related information of each customer comprises, e.g., his or her name, address, age, sex, account's type, number, and balance, and automatic-transfer payee's and payer's accounts.

In the present embodiment, the cuff 16, pump 46, valve 44, motor 50, sensor 42, filters 54, 60, and microcomputer 56 cooperate with other elements to serve as a measuring device which obtains physical information such as blood pressure and pulse rate from a living subject. The physical-information memory area 88 of the storage device 86 serves as a memory device which accumulatively stores, each time the measuring device obtains physical-information of a registered subject, the obtained physical-information of the subject, in association with his or her ID data registered in the ID data memory area 89 of the storage device 86. The microcomputer 56 or CPU 62 identifies whether or not the ID data read by the card reader 74 is the same as any of the sets of ID data registered in the ID data memory area 89. Subject to a positive identification of the CPU 62, the physical information of the subject currently obtained by the measuring device is stored in the memory area 88, and the collected, i.e., accumulatively stored physical information of the subject including the currently obtained information is read from the memory area 88 and printed on a record sheet 94 (FIG. 4) by the printer 26 which serves as an output device.

Hereinafter, there will be described the operation of the present physical-information collecting system constructed as described above, by reference to the flow charts of FIG. 3(a), FIG. 3(b), and FIG. 4.

Figure 3A:
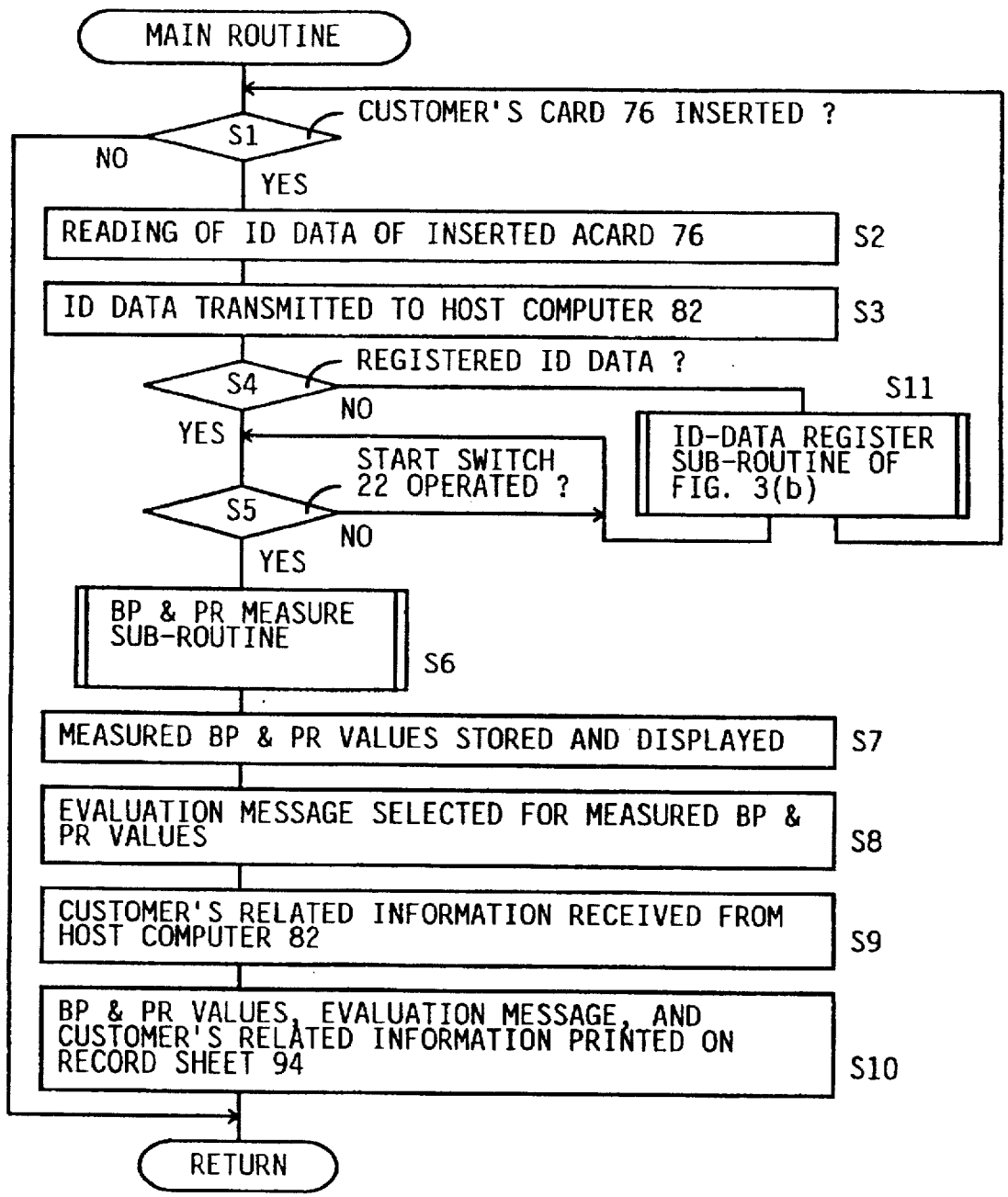
FIG. 3(a) is a flow chart representing the main control program according to which the collecting system of FIG. 1 is operated.
Figure 3:
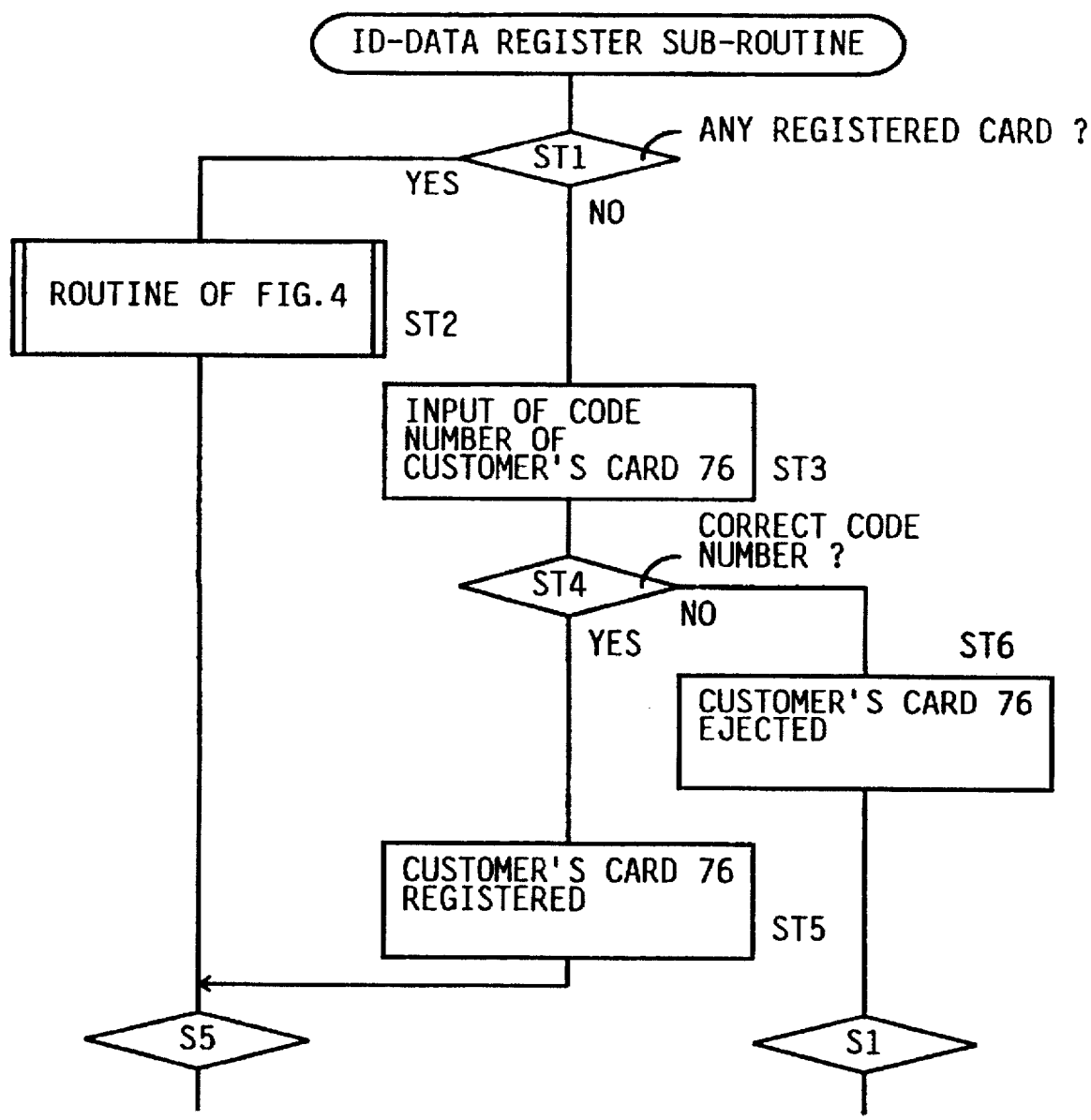
FIG. 3(b) is a flow chart representing a part of the main routine of FIG. 3(a)

First, at Step S1 of FIG. 3(a), the CPU 62 judges whether a magnetic card 76 has been inserted into the card reader 74 through the insertion slot 28. If a negative judgment ("NO") is made at Step S1, this routine is ended. On the other hand, if a positive judgment ("YES") is made, i.e., if a magnetic card 76 is inserted, the control of the CPU 62 proceeds with Step S2 to read ID data magnetically recorded on the magnetic card 76.

The magnetic card 76 may be a product according to Japanese Industrial Standard, X 6301 or X 6302. More specifically, the magnetic card 76 may be one of (a) a credit card, (b) a hospital's consultation card, (c) a bank's cash card, and (d) a health care card. Each of the first and second cards (a), (b) has a single track of data memory area in the back face thereof; the third card (c) has a single track of data memory area in the front face thereof; and the fourth card (d) has double tracks of data memory areas in the back face thereof. For example, a bank's cash card has various data recorded thereon which include respective codes of the bank, branch, related account, and number of the related account. In this case, the respective codes of the bank and related account and the number of the related account serve as ID data identifying a customer carrying the cash card. Meanwhile, a health care card has data including the code of the related company, the date and time of initialization of the card, and the serial number assigned to the card at the time of initialization. In this case, the date and time of initialization of the card and the serial number assigned to the card, provide ID data identifying the person having the magnetic card.

Step S2 is followed by Step S3 to transmit the ID data read from the magnetic card 76, to the host computer 82, and at the following Step S4 the CPU 62 identifies whether or not the ID data is registered in the apparatus 8, i.e., is the same as any of the sets of ID data registered in the ID data memory area 89 of the storage device 86. If a negative identification is made at Step S4, the control of the CPU 62 goes to the card register routine of Step S11, which is shown in FIG. 3(b).

Figure 4:
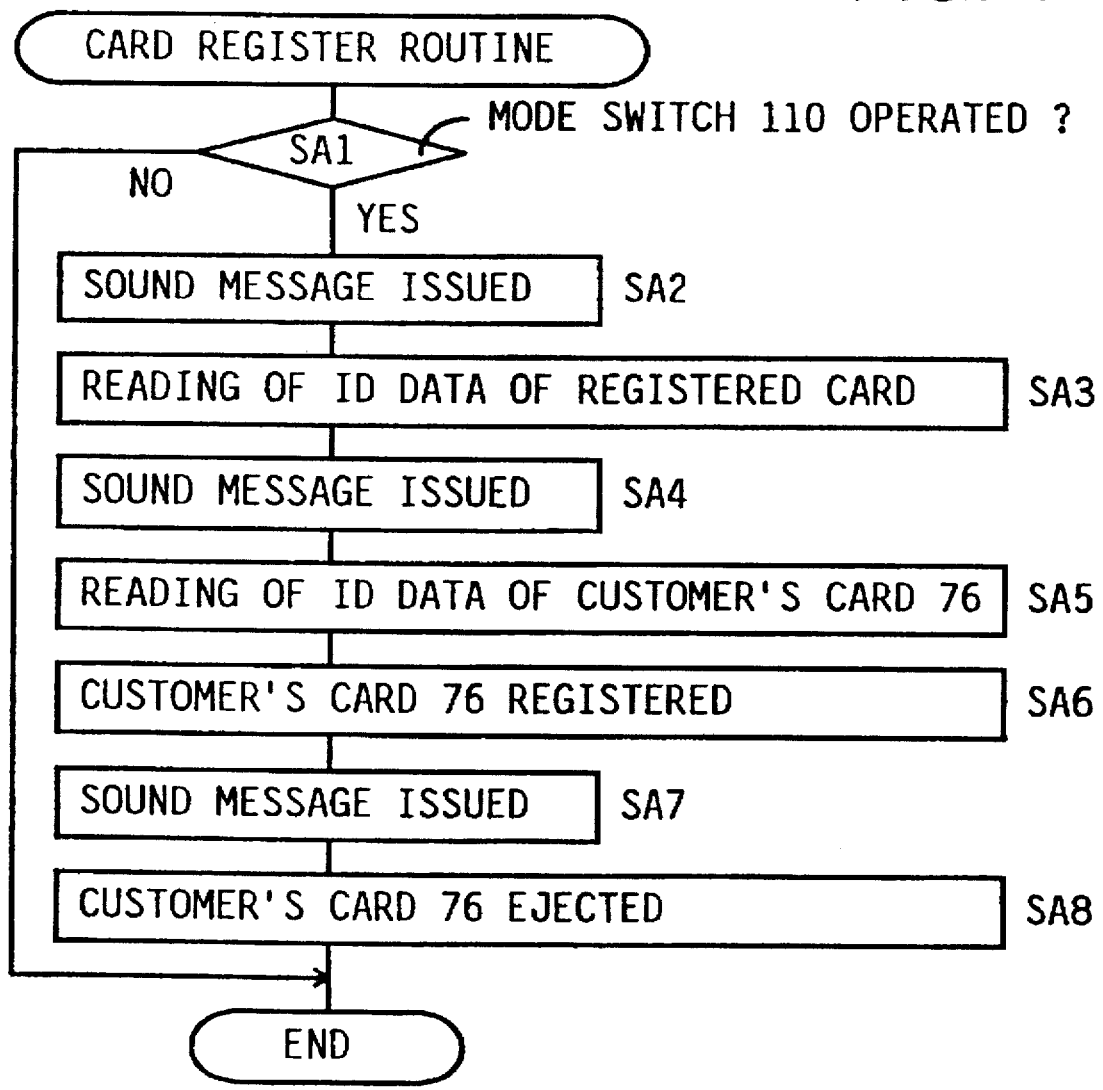
FIG. 4 is a flow chart representing the card register routine according to which a non-registered card is registered in the BP measuring apparatus of FIG. 1.

First, at Step ST1 of FIG. 3(b), the CPU 62 commands the speaker 40 to issue a sound message "DO YOU HAVE ANY CARD REGISTERED IN THIS MACHINE ?" If the customer presses by his or her finger the symbol "YES" indicated on the display panel 30, the control of the CPU 62 goes to the sub-routine of Step ST2, which is shown in FIG. 4. On the other hand, the customer presses the symbol "NO" on the display panel 30, the control of the CPU 62 goes to Step ST3 to command the speaker 40 to issue a message "PLEASE ENTER CODE NUMBER OF THE CASH CARD 76". When the customer enters, e.g., a four-digit code number by pressing the appropriate numerals "0" to "9" displayed on the display panel 30, Step ST3 is followed by Step ST 4 to judge whether the entered code number identifies the magnetic card 76 currently being inserted in the card reader 74. If a positive judgment is made at Step ST4, the control of the CPU 62 goes to Step ST5 to register the ID data of the cash card 76 in the memory area 89 of the storage device 86. Thus, the "non-registered" card 76, i.e., the "non-registered" customer carrying the card 76 is registered in the measuring apparatus 8. Then, the control of the CPU 62 goes to Step S5 of FIG. 3(a). On the other hand, if a negative judgment is made at Step ST4, the control goes to Step ST6 to commands the card reader 74 to eject the non-registered card 76, and the control of the CPU 62 returns to Step S1 of FIG. 3(a).

Meanwhile, at Step SA1 of FIG. 4, the CPU 62 commands the card reader 74 to eject the non-registered card 76, commands the speaker 40 to issue a message "PLEASE OPERATE CARD-REGISTER-MODE KEY 110", and judge whether the mode key 110 on the operation panel 20 has been operated. If a negative judgment is made at Step SA1, this routine is ended, and the control of the CPU 62 goes back to Step S1 of FIG. 3(a). On the other hand, if the customer operates the mode key 110 and a positive judgment is made at Step SA1, the control of the CPU 62 goes to Step SA2 to command the speaker 40 to issue a message "PLEASE INSERT REGISTERED CARD". Step SA2 is followed by Step SA3 to read ID data recorded on the registered card. At the following Step SA4, the CPU 62 commands the speaker 40 to issue a message "PLEASE INSERT NON-REGISTERED CARD". Step SA4 is followed by Step SA5 to read the ID data of the non-registered card 76.

Step SA5 is followed by Step SA6 to register the ID data of the magnetic card 76 and thereby register the cash card 76, by storing the ID data of the card 76 in the memory area 89 in association with the ID data of the registered card read at Step SA3. At the following Step SA7, the CPU 62 commands the speaker 40 to sound a message "YOUR CARD HAS BEEN REGISTERED IN THIS MACHINE". Step SA7 is followed by Step SA8 to eject both the registered card and the newly registered card 76. Then, the control of the CPU 62 returns to Step S1 of FIG. 3(a).

Meanwhile, if a positive identification is made at Step S4, the control of the CPU 62 goes to Step S5 to judge whether the START switch 22 has been operated to start the BP and PR measurement. The CPU 62 repeats Step S5 till a positive judgment is made. When a positive judgment is made at Step S5, the control goes to the BP and PR measure routine of Step S6 wherein the systolic, diastolic and mean blood pressure values and pulse rate value of the customer 12 are measured. In this routine, the inflatable cuff 16 is automatically inflated according to the specific control program pre-stored in the ROM 64, so that the cuff pressure represented by the electric signal SK increases up to a predetermined level. While the cuff pressure gradually decreases from the predetermined level, the CPU 62 determines the BP values by the well-known oscillometric method. For example, the systolic and diastolic BP values are determined based on variation in amplitude of respective pulses of the pressure pulse wave represented by the electric signal SM, and the mean BP value is determined as being equal to a cuff pressure SK at the time of occurrence of a pulse having a maximum amplitude. The PR value may be determined based on a time difference between two successive pulses of the pressure pulse wave SM.

Step S6 is followed by Step S7 to store, in the physical-information memory area 88 of the storage device 86, data indicative of the BP and PR values determined at Step S6, together with data indicative of the date and time of measurement of those values, in association with the registered ID data identifying the magnetic card 76 currently being inserted in the card reader 74 and thereby identifying the customer carrying the card 76. Additionally, the CPU 62 commands the SYS, DIA, and PR displays 32, 34, 36 to indicate the determined systolic and diastolic BP values and PR value, respectively. At the following Step S8, the CPU 82 selects one or more of the evaluation comments pre-stored in the memory area 87 of the storage device 86, such that the selected one or more comments correspond to the BP and PR values determined in the current measurement operation and the collected BP and PR values of the customer stored in the memory area 88.

Figure 5:
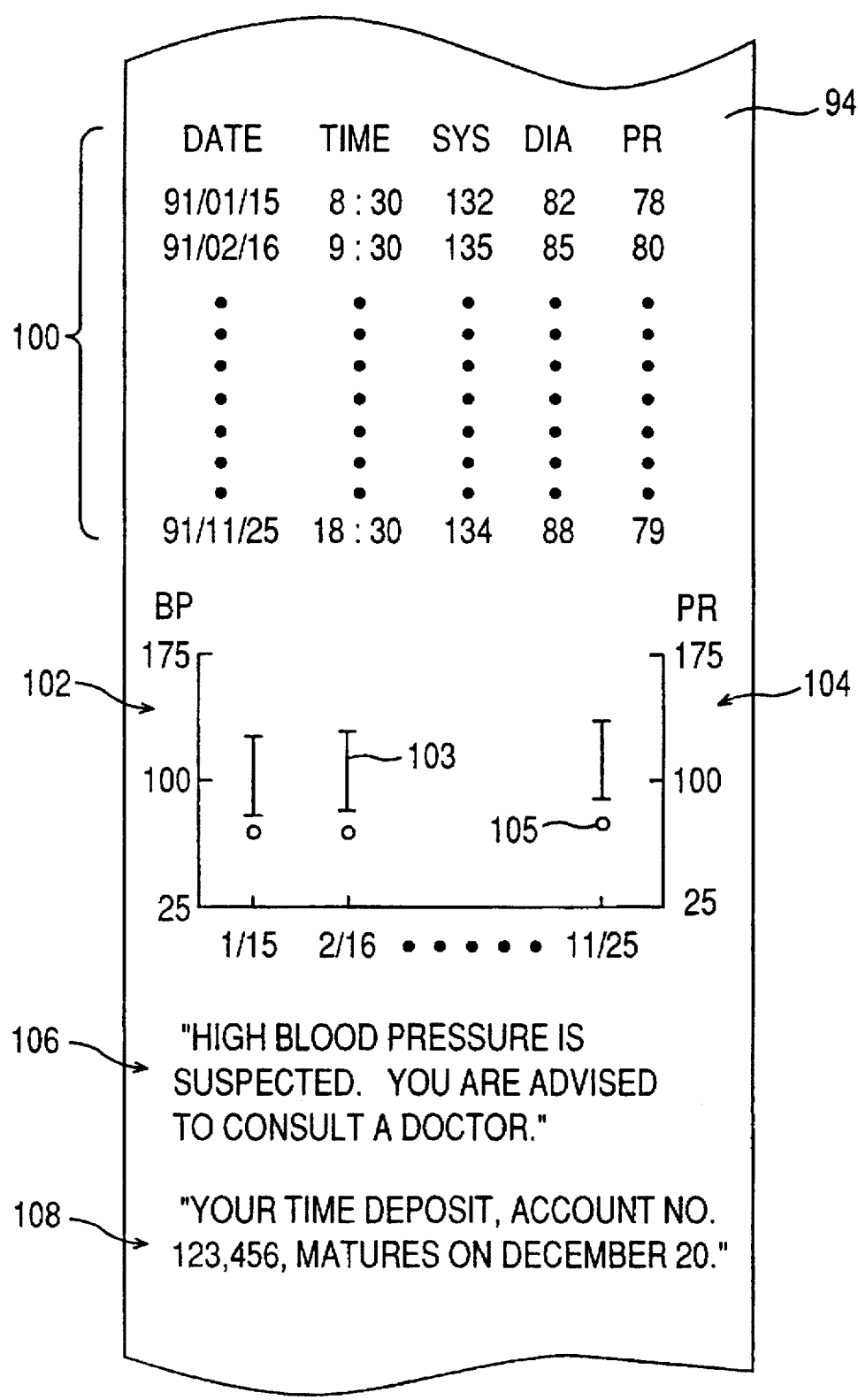
FIG. 5 is a view of a record sheet as an output of the collecting system of FIG. 2.

Step S8 is followed by Step S9 to make access to the host computer 82 to receive the information related to the customer identified by the ID data read at Step S2. The host computer 82 specifies the name of the customer based on the ID data supplied from the CPU 62 at Step S3, and transmits useful information related to the customer, e.g., date when his or her time deposit matures and/or new banking service suitable to the customer. At the next step, Step S10, the CPU 62 commands the printer 26 to output a recorded sheet 94 as shown in FIG. 5. The printer 26 records, on the sheet 94, (a) a data table 100 including the date and time, SYS and DIA BP values, and PR value for each of the measurements stored in the memory area 88, (b) a BP graph 102 representing a chronological change of BP values of the customer 12, (c) a PR graph 104 representing a chronological change of PR values of the same 12, (d) an evaluation comment 106 selected for the above information (a) to (c), and (d) non-physical information 108 related to the customer 12. Specifically, regarding the BP graph 102, the upper and lower ends of each bar 103 indicate the SYS and DIA blood pressure values, respectively, and successive bars 103 are associated with their measurement dates marked along the axis of abscissa of the graph 102. Regarding the PR graph 104, each PR value is indicated by a small circle associated with its date marked along the axis of abscissa of the graph 104 shared by the BP graph 102.

Meanwhile, the card register routine of FIG. 4 may be used independent of the main routine of FIG. 3(a), for registering a magnetic card which is not registered in the apparatus 8 of FIG. 1. To this end, the card-register-mode switch 110 is first operated by a customer without inserting any magnetic card in the card reader 74 before. By utilizing this function, a plurality of personal cards of an identical person can be registered in the apparatus 8, so that the person can operate the apparatus 8 by using one of the registered cards.

As is apparent from the foregoing description, in the present physical-information collecting system, the physical information (i.e., BP and PR values) of a customer stored in the physical-information memory area 88 of the storage device 86 cannot be accessed by other persons, unless his or her registered card is used by those persons. Thus, the present system protects the privacy of the customer with high reliability.

Additionally, the present collecting system has the function of selecting, and outputting, one or more evaluation comments 106 which correspond to the physical information obtained by the measuring apparatus 8 in the current operation and/or the history or accumulation of physical information stored in the physical-information memory area 88. This system is more advantageous than the conventional BP measuring device wherein only the BP value and/or BP change is or are outputted. This evaluation is very useful for health care of customers.

Furthermore, the present collecting system has the function of reading, from the host computer 82, non-physical information 108 related to the customer 12 who has inserted the magnetic card 76 into the card reader 74, and outputting the related information 108 on the recording sheet 94. In the case where the related information 108 include, e.g., date when the time deposit of the customer 12 matures, he or she may be informed of it, though the date is likely forgotten.

Figure 6:
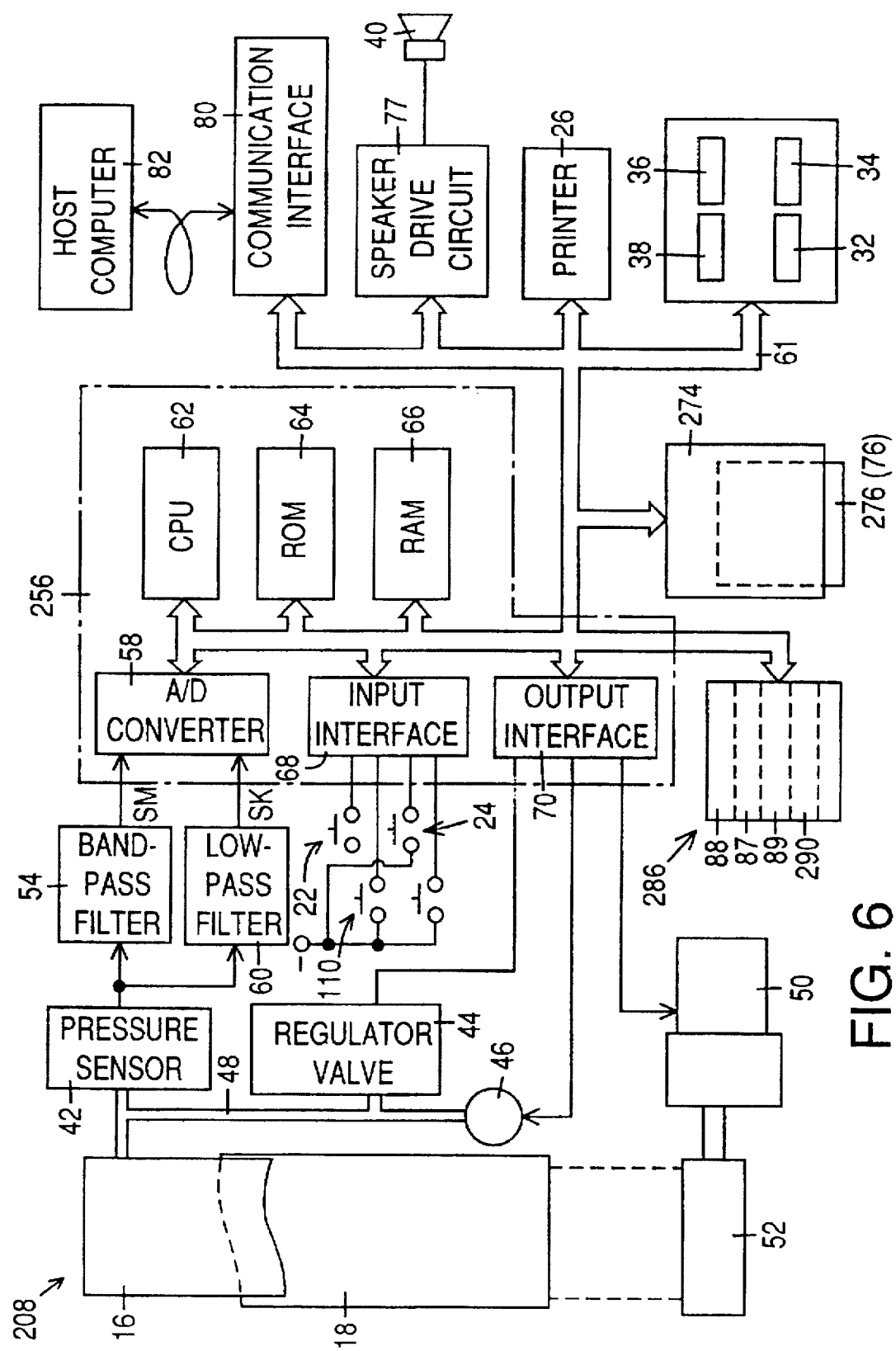
FIG. 6 is a diagrammatic view of the electric construction of another physical-information collecting system as a second embodiment of the present invention.

Referring next to FIG. 6, there is shown the second embodiment of the present invention which has generally the same hard-ware construction as that of the first embodiment shown in FIGS. 1 and 2. Therefore, in the following description of the second embodiment, the same reference numerals as used for the first embodiment in FIGS. 1 and 2 are used for designating the corresponding elements or parts of the second embodiment in FIG. 6, and only the differences between the two embodiments will be described below.

Figure 8:
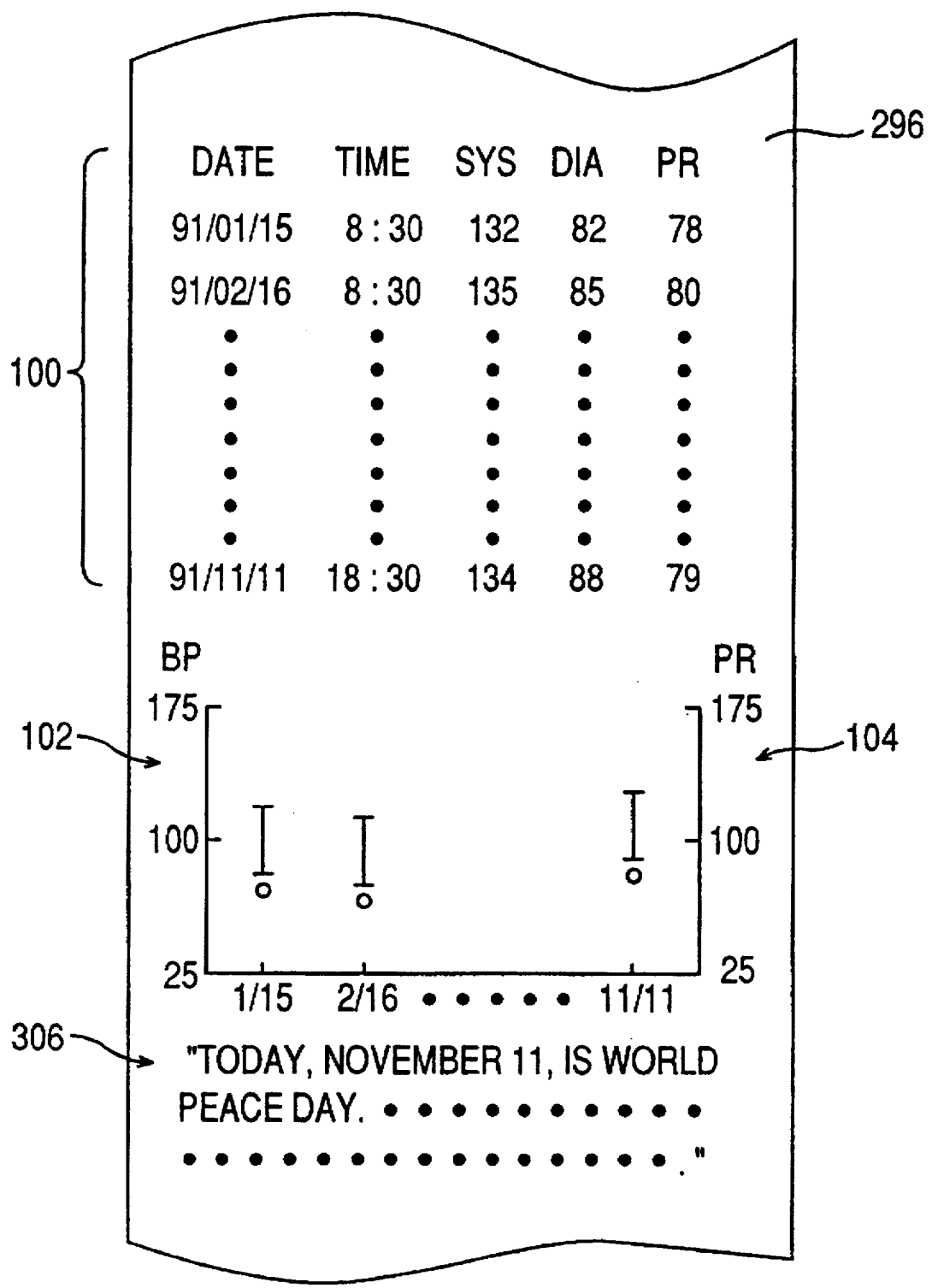
FIG. 8 is a view of a record sheet as an output of the collecting system of FIG. 6.

The physical-information collecting system of FIG. 6 includes an automatic BP measuring apparatus 208. The apparatus 208 includes a blood pressure measuring device 16, 42, 44, 46, 54, 60, a microcomputer 256, and a storage device 286. The storage device 286 includes, in addition to (a) a physical-information memory area 88, (b) an evaluation-comment memory area 87, and (c) an ID-data memory area 99, (d) a mini-information memory area 290 for storing non-physical "mini" information such as short and useful knowledge, proverb, slogan, motto, short verse (e.g., Japanese 17- or 35-syllable verse), etc. The mini information may be a set of image data representing a predetermined image. The CPU 62 generates record signal based on the mini information stored in the memory area 290, and feeds the record signal to a printer 26 to record a mini information (i.e., predetermined image) 306 on a record sheet 296 (FIG. 8). The microcomputer 256 commands a card reader 274 to read mini information magnetically recorded on a mini-information card 276, and stores the read mini information in the memory area 290 of the storage device 286. The card 276 bears, on the front surface thereof, the same mini information (i.e., predetermined image) printed in the form of, i.e., a short sentence as that magnetically recorded thereon, so that the user can readily identify, from the front surface of the card 276, the mini information recorded thereon.

Figure 7:
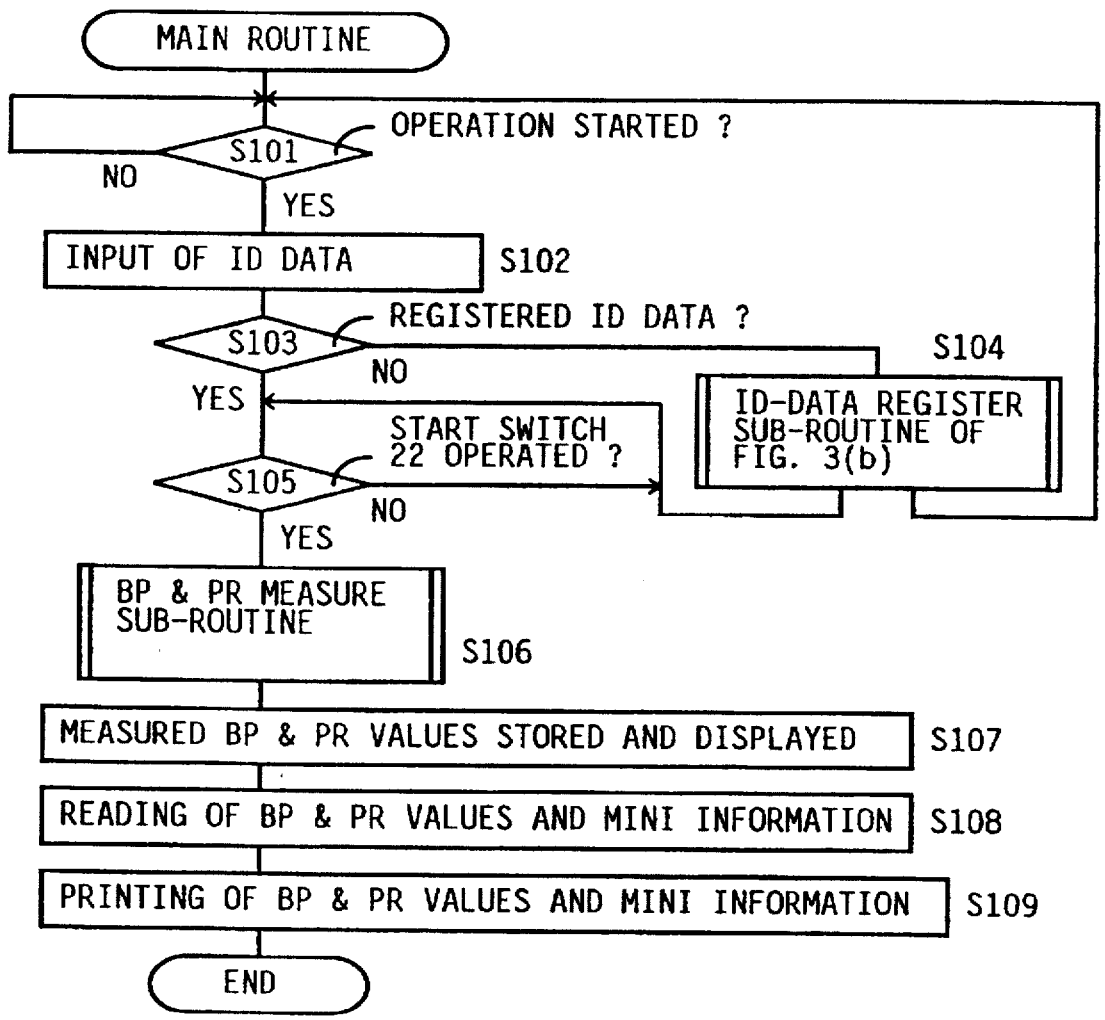
FIG. 7 is a flow chart representing the main control program according to which the collecting system of FIG. 6 is operated.

The instant collecting system is operated according to the control program represented by the flow chart of FIG. 7. The control program is pre-stored in a ROM 64 of the microcomputer 256.

First, at Step S101, the CPU 62 judges whether the operation of the collecting system has been started. For example, when a personal card 76 (e.g., bank's cash card) is inserted into a card insertion slot 28 of the card reader 274, or when a main switch (not shown) is operated, a positive judgment is made at Step S101. The CPU 62 repeats Step S101 until a positive judgment is made and, in response to a positive judgment, the control of the CPU 62 proceeds with Step S102 to read ID data recorded on the personal card 76, or wait for ID data being entered by a customer through a display panel 30.

Step S102 is followed by Step S103 to judge whether the ID data read or entered at Step S102 is the same as any of the sets of ID data which are registered in the apparatus 208, i.e., stored in the ID data memory 89 of the storage device 286. If a negative judgment is made at Step S103, the control of the CPU 62 goes to the sub-routine of Step S104. In the case where the ID data is read from the personal card 76, the sub-routine of Step S11 of FIG. 3(a) (represented by the flow chart of FIG. 3(b)) is effected. Meanwhile, in the case where the ID data is entered by the customer through the display panel 30, the ID data is registered in the memory area 89. Thus, in the instant embodiment, the ID data registered at Step S104 may originate either from the ID data recorded on the personal card 76 or from the ID data directly entered by the customer. On the other hand, if a positive judgment is made at Step S103, the control of the CPU 62 goes to Step S105 and the following steps S106 to S109. Since Steps S105, S106, and S107 are the same as Steps S5, S6, and S7 of FIG. 3(a), respectively, the description thereof is omitted.

At Step S108, the CPU 62 reads the physical information accumulatively stored in the physical-information memory area 88 of the storage device 286, and reads the mini information stored in the mini-information memory area 290 of the same 286. Step S108 is followed by Step S109 to command the printer 26 to record, on the record sheet 296, the mini information 306 together with a data table 100, a BP graph 102, and a PR graph 104, as shown in FIG. 8. In the instant embodiment, the physical information 100, 102, 104 and the mini information 306 are concurrently outputted by the common output means, i.e., printer 26.

Figure 9:
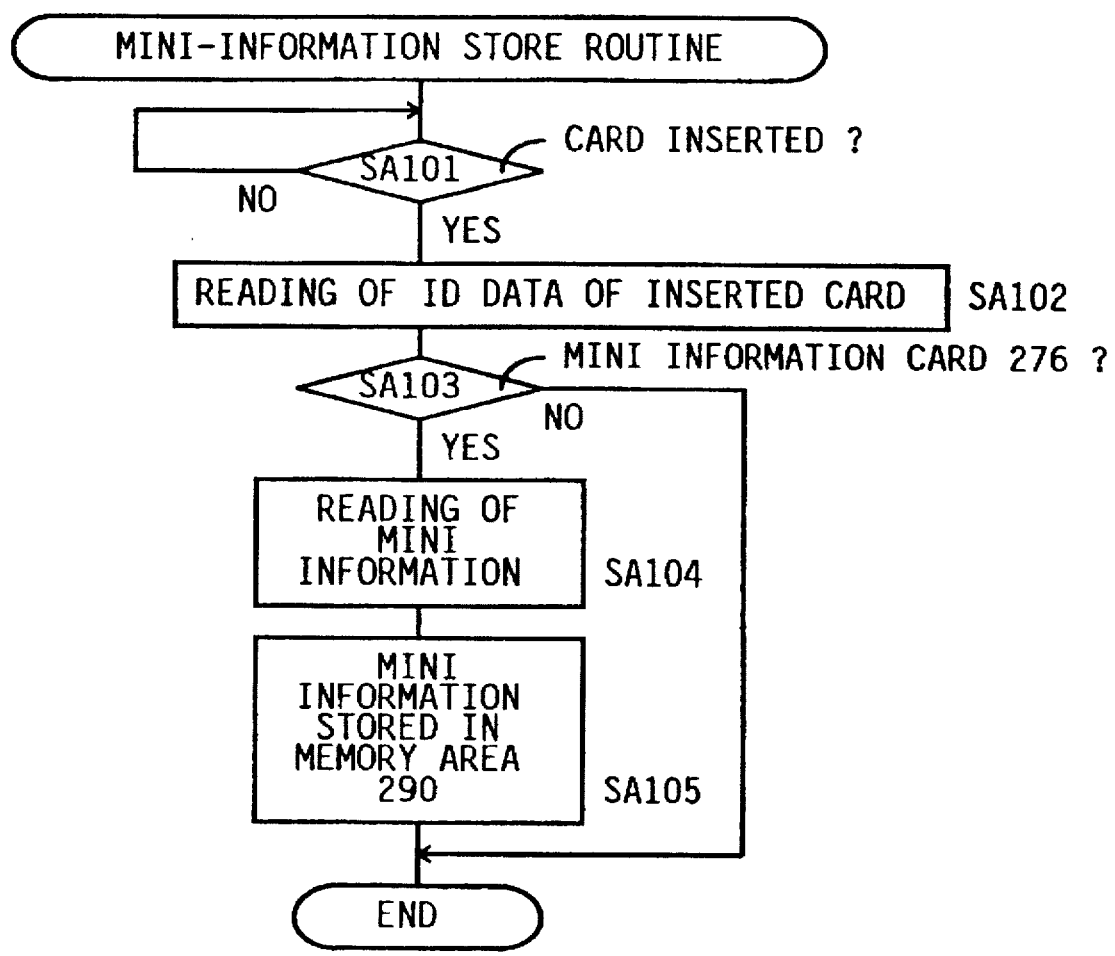
FIG. 9 is a flow chart representing the mini-information store routine according to which mini information is stored in an automatic BP measuring apparatus of the collecting system of FIG. 6.

The CPU 62 operates, according to the mini-information store routine shown in FIG. 9, for commanding the card reader 274 to read the mini information from the mini information card 276 being inserted therein and store the read mini information in the memory area 290 of the storage device 286. The mini information card 276 may be a product according to Japanese Industrial Standard, X 6301 or X6302. In this case, the card 276 has a single or double tracks of data memory area or areas in the front or opposite face thereof. Usually, a plurality of mini information cards 276 are kept by the bank, and an appropriate one of them is selected and inserted into the card reader 274 to read and store the mini information recorded thereon. The cards 276 have different pieces of mini information (e.g., different sets of image data) respectively recorded thereon, and one of opposite surfaces of each card 276 bears a corresponding piece of mini information printed thereon, so that the user may easily specify and select a desired one from the many cards 276. The routine of FIG. 9 is effected concurrently with the routine of FIG. 7.

Specifically, first, at Step SA101, the CPU 62 judges whether a magnetic card 76 or 276 has been inserted into the card insertion slot 28 of the card reader 274. The CPU 62 repeats Step SA101 until a positive judgment is made and, in response to a positive judgment, the control of the CPU 62 goes to Step SA102 to read ID data recorded on the magnetic card 76, 276. Step SA102 is followed by Step SA103 to judge whether the ID data read at Step SA102 identifies a mini information card 276. If a negative judgment is made at Step SA103, this routine is ended. On the other hand, if a positive judgment is made, the control of the CPU 62 goes to Step SA104 to read, from the card 276, the mini information recorded thereon which is to be printed on a record sheet 296. Step SA104 is followed by Step SA105 to store the read mini information in the memory area 290 of the storage device 286.

As is apparent from the foregoing description, the mini information 306 to be recorded on the record sheet 296 is easily changed with another, by changing the mini information cards 276 and inserting a new one in the card reader 276.

Figure 10:
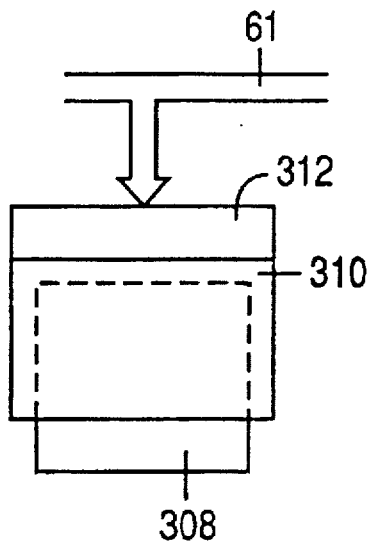
FIG. 10(a) is a view of a card reader which is connected to the BP measuring apparatus of the collecting system of FIG. 6 and which is used for selecting and reading one of a plurality of pieces of mini information stored in a mini-information card.
FIG. 10(b) is a view of another card reader which is connected to a host computer of the collecting system of FIG. 6 and which is used for selecting and reading one of a plurality of pieces of mini information stored in a mini-information card.
Figure 10:
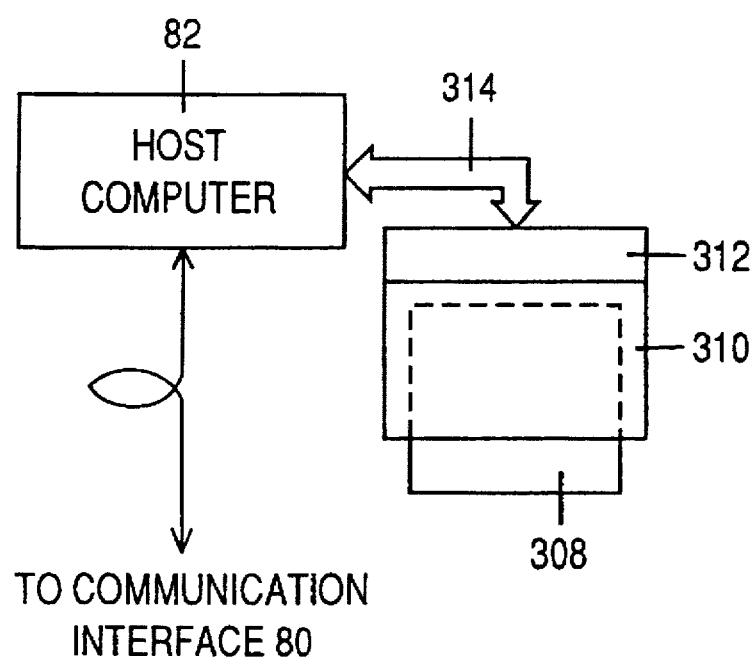

While the second embodiment relates to the collecting system adapted for use with the mini information card or cards 276 each of which has a single piece of mini information recorded thereon, it is possible to adapt the collecting system for use with a mini information card 308 (e.g., IC card) in which different pieces of mini information are electrically recorded, as shown in FIG. 10(a) or 10(b). FIG. 10(a) shows a first modified arrangement wherein the measuring apparatus 208 is provided with an exclusive card reader 310 for reading mini information from the IC card 308, while FIG. 10(b) shows a second modified arrangement wherein the host computer 82 is provided with an identical card reader 310. The card reader 310 is connected to the apparatus 208 or host computer 82 via (a) an input interface 312 and (b) bus 61 or bus 314. Regarding the second arrangement of FIG. 10(b), the mini information read from the IC card 308 is transmitted to the apparatus 208 via a communication interface 80, and stored in the memory area 290 of the storage device 286.

Figure 11:
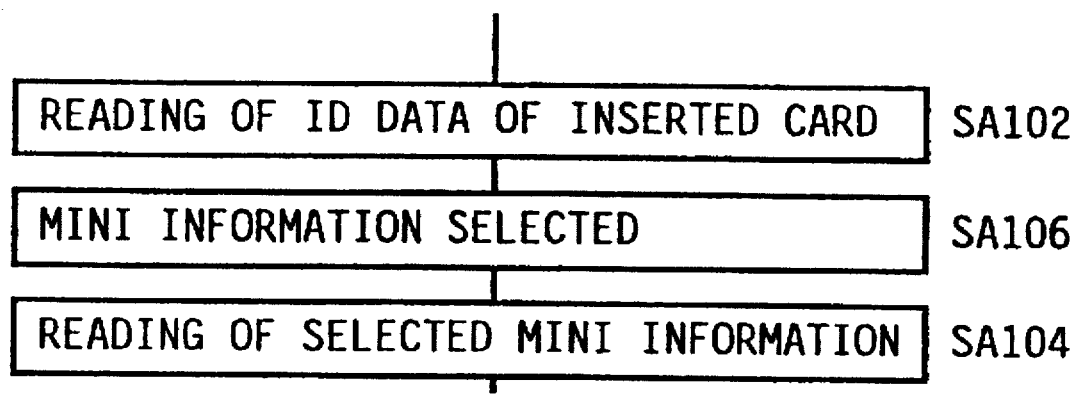
FIG. 11 is a flow chart corresponding to a portion of the flow chart of FIG. 9, according to which the card reader of FIG. 10(a) or 10(b) reads a selected one piece of mini information from a mini-information card.

For each of the above-described two modified arrangements wherein the card reader 310 is employed, Step SA106 is effected as shown in FIG. 11, in place of Step SA103 of FIG. 9. At Step SA106, the CPU 62 selects or specifies one of the different pieces of mini information recorded on the IC card 308, and at the following Steps, SA104 and SA105, the CPU 62 reads the selected mini information from the IC card 308 and stores the read mini information in the memory area 290. On the IC card 308, each piece of mini information may be recorded in association with a corresponding date or a corresponding sequential number. In the latter cases, the different pieces of mini information are automatically read one by one by the CPU 62 from the IC card 308 according to the calendar (i.e., dates) or the sequential numbers. In those arrangements, the mini information 306 to be recorded on the record sheet 296 is automatically changed with another, by simply inserting the IC card 308 in the card reader 310 connected to the apparatus 208 or host computer 82. Thus, the time necessary to specify and select one of the different mini-information cards 276 is advantageously saved.

Figure 12:
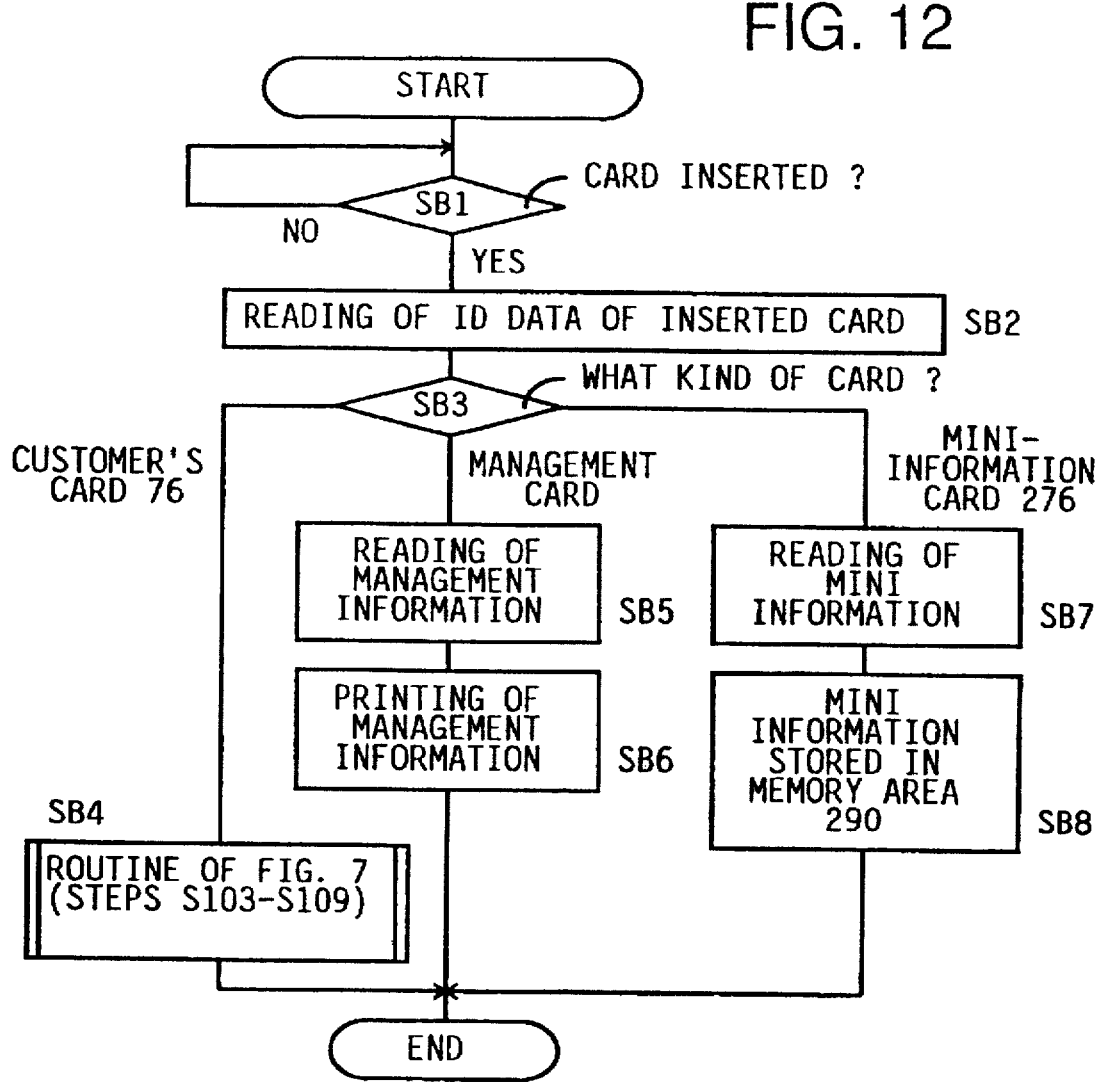
FIG. 12 is a flow chart representing the main control program according to which a physical-information collecting system as a third embodiment of the present invention is operated.

Referring next to FIG. 12, there will be illustrated a third embodiment of the present invention. In the third embodiment, the flow chart of FIG. 7 used in the second embodiment of FIG. 6 is modified as indicated by the flow chart of FIG. 12. As previously described, in the second embodiment, the physical information obtained by the measuring apparatus 208 is stored in the memory area 288, together with operation data (e.g., date and time of measurement) as part of the physical information of the customer. The operation data may be utilized for bank's management of its customers. It is useful for a managerial or authorized person to make access to those operation data independent of the other physical information (e.g., BP and RP values) of the customers. The flow chart of FIG. 12 provides the function of identifying (a) ID data recorded on a management card carried by the authorized person, (b) ID data recorded on the cash card 76 carried by the customer, and (c) ID data recorded on the mini-information card 276, from each other. In the third embodiment, the measuring apparatus 208 is operated according to the flow chart of FIG. 12, as follows:

Steps SB1 and SB2 are the same as Steps SA101 and SA102 of FIG. 7, respectively, and the description thereof is skipped. At Step SB3, the CPU 62 identifies the kind or sort of the ID data read from a card inserted at Step SB2. In the case where the read ID data identifies a bank's customer, the control of the CPU 62 proceeds with Step SB4 where the CPU 62 carries out Steps S103 through S109 of the routine of FIG. 7. In the case where the read ID data identifies an authorized person of the bank, i.e., is found as the special data recorded on the management card, the control of the CPU 62 goes to Step SB5 to read the operation data, such as the daily number of customers having used the apparatus 208 and/or the records of use of individual customers, from the physical-information memory area 288 of the apparatus 208. Step SB5 is followed by Step SB6 to command the printer 26 to output a record sheet 396 as shown in FIG. 13. The record sheet 396 bears a data table 422 indicating the records of use of individual customers, a graph 424 representing the daily numbers of "measured" customers along with the dates. On the other hand, in the case where the read ID data identifies a mini-information card 276, the control of the CPU 62 goes to Steps SB7 and SB8 that are the same as Steps SA104 and SA105 of FIG. 9. At Step SB8, the CPU 62 stores, in the memory area 290, the mini information read from the card 276 at Step SB7.

In the third embodiment, a non-physical mini information 306 is printed together with the stored physical information on a record sheet 396 issued for a customer, like in the second embodiment. The mini information 306 is easily changed with another by inserting, into an insertion slot 28 of a card reader 274, a different mini-information card in place of the current card 276 being inserted in the slot 28.

Similar to the flow chart of FIG. 7 used in the second embodiment, the flow chart of FIG. 3(a) used in the first embodiment may be modified as indicated in FIG. 12. In this case, however, Steps SB7 and SB8 are omitted and, at Step SB4, Steps S3 through S11 of FIG. 3(a) are carried out.

In the above modified arrangement of the first or second embodiment, an authorized person such as a bank's managerial person can obtain the operation data such as the records of use of individual customers and the number of measurements per day, simply by inserting the management card in the apparatus 208. The thus obtained management information is useful for bank's management of its customers.

While the present invention has been described in its preferred embodiments, the present invention may otherwise to be embodied.

For example, although the physical-information collecting system of FIG. 6 may be used with the card reader 310 which is adapted to automatically select and read one of the plurality of pieces of mini information recorded on the IC card 308, it is also possible to connect a keyboard (not shown) to the collecting system so that a desired piece of mini information can be selected and read from the IC card 308 by operating the keyboard.

In place of the IC card 308, it is possible to employ, as a data-storage medium, various sorts of disks such as a compact disk (CD), magnetic disk, or photo-magnetic disk, or alternatively use a magnetic tape. In those cases, in place of the card reader 310, a different data reading device is used for reading data from a corresponding data-storage medium. Additionally, at Steps SA101 and SA102 of FIG. 11, the data-storage medium may be set in the data reading device, in place of inserting the card 308, and ID data recorded on the medium may be read in place of reading the ID data of the card 308.

While in the second embodiment of FIG. 6 the non-physical mini information or predetermined image 306 is printed on the record sheet 296 together with the stored physical information of the customer, the output of the mini information may be effected in a different manner. For example, the mini information may be issued as a sound message through the speaker 40. Otherwise, it may be displayed by a liquid crystal or light emitting diode (LED) provided in the display panel 30. The physical information and the mini information may be outputted by different output means, respectively, so long as the two kinds of information are produced in a single or common operation cycle for the living subject 12.

Although in the third embodiment of FIG. 12 the operation data of the apparatus 208 are stored as part of the physical information of the customers in the memory area 288 of the data-storage device 286, it is possible to prepare, in the storage device 286, an exclusive memory area for storing the operation data of each of the subjects in association with the physical information of each subject stored in the memory area 288.

While in the second or third embodiment the card reader 274 is connected to the measuring apparatus 208, a similar card reader may additionally be connected to the host computer 82, so that the mini information card 276 or management card can be inserted in the card reader connected to the host computer 82.

In the second embodiment of FIG. 6, it is possible to employ, as the data-storage device 286, a memory whose capacity is considerably small, by storing the physical information and ID data of the customers in a date-storage device provided in the host computer 82. In this case, one step is added after Step S102 to transmit the ID data read at this step, to the host computer 82, so that the host computer 82 identifies whether the ID data transmitted is the same as any of the registered sets of ID data stored in the data-storage device of the computer 82. Additionally, at Steps S107 and S108, the host computer 82 stores the obtained physical information of the customer in the data-storage device thereof and reads the collected physical information of the customer from the data-storage device. In the third embodiment, a similar step is added before Step SB4 or Step SB5 to transmit the ID data identifying the customer, or the special ID data identifying the bank's managerial person, to the host computer 82 so that the host computer 82 reads the physical information of the customer, or the operation data relating to the operation of the apparatus 208 from the data-storage device of the host computer 82.

On the record sheet 296 shown in FIG. 8 as an output of the collecting system of FIG. 6, it is possible to print an evaluation comment 106 and a customer's related information 108 as shown in FIG. 5, in addition to the physical information 100–104 and the mini information 306.

The magnetic card 76 used with the illustrated collecting systems is not limited to the previously described ones such as a bank's cash card 76 or management card but may be a post office's or agricultural cooperative's card, or alternatively a driver's licence card on which ID data of the driver is magnetically recorded. Otherwise, in place of the magnetic personal card 76, it is possible to employ a card on which ID data is mechanically recorded, or an integrated circuit (IC) card on which ID data is electrically recorded.

While the illustrated collecting systems relate to the BP & PR measuring apparatus 8, 208, the present invention is applicable to other physical-information obtaining devices which measure, e.g., weight, height, body fat percentage, or arterial sclerosis degree of a living subject. In those cases, the measured weight, height, or body fat percentage value may be displayed together with an evaluation comment such as "YOUR BODY FAT PERCENTAGE, 26%, IS RATHER HIGHER THAN AVERAGE. FOR THIS YOUR DIASTOLIC PRESSURE AND PULSE RATE ARE ABOVE AVERAGES. YOU ARE ADVISED TO REDUCE YOUR WEIGHT TO 63 KILOGRAMS".

Although the illustrated collecting systems have been described where those systems are used in a bank's office, the invention systems may advantageously be used in other facilities such as a post office, life insurance company, securities company, or athletic gym or club.

It is to be understood that the present invention may be embodied with other changes, improvements, and modifications that may occur to those skilled in the art without departing from the scope and spirit of the invention defined in the appended claims.

What is claimed is:

1. A physical-information collecting system for collecting physical information of a plurality of living subjects, comprising:

an identification data registering device which registers a plurality of sets of identification data each of which identifies a corresponding one of said living subjects;

a card reading device into which a personal card having a set of identification data is inserted by a living subject, said card reading device reading said set of identification data from said personal card inserted therein;

identification data identifying means for identifying whether said set of identification data read by said card reading device is same as one of said sets of identification data registered in said identification data registering device;

a measuring device which obtains physical information from said living subject who has inserted said personal card into said card reading device;

a first memory device which stores, each time said measuring device obtains physical information from said living subject, the obtained physical information of said living subject, subject to a positive identification of said identification data identifying means that said set of identification data read by said card reading device is same as one of said sets of identification data registered in said identification data registering device; and an output device which outputs, in response to said positive identification of said identification data identifying means, the physical information of said living subject accumulatively stored in said first memory device and does not output the physical information accumulatively stored in the first memory device for other living subjects identified by the other sets of identification data registered in said identification data registering device.

2. A physical-information collecting system according to claim 1, wherein said identification data registering device comprises a register mode select device which is operable for establishing a register mode in which, when said card reading device reads a plurality of sets of identification data from a plurality of personal cards including a registered personal card whose identification data is registered in said identification data registering device, said identification data registering device registers said sets of identification data read by said card reading device such that each of the thus registered sets of identification data identifies an identical person identified by the identification data of said registered personal card, said identification data identifying means providing said positive identification when said set of identification data read by said card reading device from said personal card of said living subject is same as one of a plurality of sets of identification data registered in said identification data registering device each of which identifies said living subject.

3. A physical-information collecting system according to claim 1, further comprising:

a second memory device which stores a plurality of sets of evaluation comment data each of which represents a corresponding one of a plurality of physical-information evaluation comments;

selecting means for selecting at least one of said evaluation comments which corresponds to at least one of (a) the physical information of said living subject accumulatively stored in said first memory device and (b) the physical information of said living subject currently obtained by said measuring device; and said output device outputting the accumulatively stored physical information of said living subject, together with said at least one evaluation comment selected by said selecting means.

4. A physical-information collecting system according to claim 1, further comprising a second memory device which stores, each time non-physical information related to each of said living subjects whose identification data are registered in said identification data registering device is produced in the collecting system, the related non-physical information of said each living subject, in association with the registered identification data identifying said each living subject, said output device outputting the physical information of said each living subject accumulatively stored in said first memory device, together with the related non-physical information of said each living subject accumulatively stored in said second memory device.

5. A physical-information collecting system according to claim 1, wherein said output device comprises at least one of (a) a printer which records, on a recording sheet, the physical information of said living subject accumulatively stored in said first memory device and (b) a display which displays the accumulatively stored physical information of said living subject.

6. A physical-information collecting system according to claim 1, wherein said measuring device measures at least one of a blood pressure and a pulse rate of said living subject.

7. A physical-information collecting system according to claim 1, wherein said card reading device reads said set of identification data magnetically recorded on said personal card of said living subject.

8. A physical-information collecting system according to claim 1, further comprising a second memory device which stores, each time said measuring device obtains physical information from each of said living subjects whose identification data are stored in said identification data registering device, operation data related to operation of the collecting system when said first memory device stores the obtained physical information of said each living subject.

9. A physical-information collecting system according to claim 8, wherein said second memory device stores, as said operation data related to said operation of the collecting system, at least one of a date and a time when said first memory device stores said obtained physical information of said each living subject.

10. A physical-information collecting system according to claim 8, further comprising:

a special data registering device which registers at least one set of special data identifying at least one special card different from said personal card of said living subject;

said card reading device reading, when one of said at least one special card is inserted thereinto, the set of special data recorded on said one special card inserted therein;

special data identifying means for identifying whether a set of data read by said card reading device is same as one of said at least one set of special data registered in said special data registering device; and an operation data output device which outputs the operation data accumulatively stored in said second memory device, subject to a positive identification of said special data identifying means that said set of data read by said card reading device is same as one of said at least one set of special data registered in said special data registering device.

11. A physical-information collecting system according to claim 1, wherein said card reading device reads, when one of a plurality of information cards each of which has a corresponding one of a plurality of pieces of non-physical information is inserted thereinto, the piece of non-physical information recorded on said one information card inserted therein, the collecting system further comprising a second memory device which stores the non-physical information read by said card reading device, said output device outputting the physical information of said living subject accumulatively stored in said first memory device together with the non-physical information stored in said second memory device.

12. A physical-information collecting system according to claim 1, further comprising:
   selecting means for selecting one of a plurality of pieces of non-physical information recorded on a recording medium;
   an information reading device which reads said one piece of non-physical information selected by said selecting means; and
   a second memory device which stores the non-physical information read by said information reading device, said output device outputting the physical information of said living subject accumulatively stored in said first memory device together with the non-physical information stored in said second memory device.

13. A physical-information collecting system according to claim 1, wherein said measuring device comprises means for obtaining circulatory-organ-related information from said living subject.

14. A physical-information collecting system for collecting physical information of a plurality of living subjects, comprising:
   an identification data registering device which registers a plurality of sets of identification data each of which identifies a corresponding one of said living subjects;
   a measuring device which obtains physical information from each of said living subjects;
   a first memory device which stores, each time said measuring device obtains physical information from said each living subject, the obtained physical information of said each living subject in association with a corresponding one of said sets of identification data registered in said identification data registering device;
   a card reading device into which one of a plurality of information cards each of which has a corresponding one of a plurality of pieces of non-physical information is inserted, said card reading device reading the piece of non-physical information recorded on said one information card inserted therein;
   a second memory device which stores the non-physical information read by said card reading device; and
   an output device which outputs the physical information of said each living subject accumulatively stored in said first memory device, together with the non-physical information stored in said second memory device.

15. A physical-information collecting system according to claim 14, further comprising:
   a special data registering device which registers at least one set of special data identifying at least one special card different from said information cards;
   said card reading device reading, when one of said at least one special card is inserted thereinto, the set of special data recorded on said one special card inserted therein;
   special data identifying means for identifying whether a set of data read by said card reading device is same as one of said at least one set of special data registered in said special data registering device;
   a third memory device which stores, each time said measuring device obtains physical information from said each living subject, operation data related to operation of the collecting system when said first memory device stores the obtained physical information of said each living subject; and
   an operation data output device which outputs the operation data accumulatively stored in said third memory device, subject to a positive identification of said special data identifying means that said set of data read by said card reading device is same as one of said at least one set of special data registered in said special data registering device.

16. A collecting system according to claim 15, wherein said third memory device stores, as said operation data related to said operation of the collecting system, at least one of a date and a time when said first memory device stores said obtained physical information of said each living subject.

17. A physical-information collecting system according to claim 14, wherein said output device comprises at least one of (a) a printer which records, on a recording sheet, the physical information of said each living subject accumulatively stored in said first memory device, together with the non-physical information stored in said second memory device, and (b) a display which displays the accumulatively stored physical information of said each living subject together with the non-physical information stored in said second memory device.

18. A collecting system according to claim 14, wherein said measuring device measures at least one of a blood pressure and a pulse rate of said each living subject.

19. A collecting system according to claim 14, further comprising:
   an input device which is operable by a living subject for inputting a set of identification data identifying said living subject; and
   identification data identifying means for identifying whether said set of identification data inputted through said input device is same as one of said sets of identification data registered in said identification data registering device.

20. A system according to claim 19, wherein said identification data registering device registers said set of identification data inputted through said input device when said identification data identifying means provides a negative identification that the inputted set of identification data is not registered in the identification data registering device.

21. A physical-information collecting system for collecting physical information of a plurality of living subjects, comprising:
   an identification data registering device which registers a plurality of sets of identification data each of which identifies a corresponding one of said living subjects;
   a measuring device which obtains physical information from each of said living subjects;
   a first memory device which stores, each time said measuring device obtains physical information from said each living subject, the obtained physical information of said each living subject in association with a corresponding one of said sets of identification data registered in said identification data registering device;
   selecting means for selecting one of a plurality of pieces of non-physical information recorded on a recording medium;
   information reading means which reads said one piece of non-physical information selected by said selecting means;
   a second memory device which stores the non-physical information read by said information reading means; and an output device which outputs the physical information of said each living subject accumulatively stored in said first memory device, together with the non-physical information stored in said second memory device.

22. A physical-information collecting system according to claim 21, further comprising:
- a special data registering device which registers at least one set of special data identifying at least one special card;
- said information reading means comprising a card reading device which reads, when one of said at least one special card is inserted thereinto, the set of special data recorded on said one special card inserted therein;
- special data identifying means for identifying whether a set of data read by said card reading device is same as one of said at least one set of special data registered in said special data registering device;
- a third memory device which stores, each time said measuring device obtains physical information from said each living subject, operation data related to operation of the collecting system when said first memory device stores the obtained physical information of said each living subject; and
- an operation data output device which outputs the operation data accumulatively stored in said third memory device, subject to a positive identification of said special data identifying means that said set of data read by said card reading device is same as one of said at least one set of special data registered in said special data registering device.

23. A physical-information collecting system according to claim 22, wherein said third memory device stores, as said operation data related to said operation of the collecting system, at least one of a date and a time when said first memory device stores said obtained physical information of said each living subject.

24. A physical-information collecting system according to claim 21, wherein said output device comprises at least one of (a) a printer which records, on a recording sheet, the physical information of said each living subject accumulatively stored in said first memory device, together with the non-physical information stored in said second memory device, and (b) a display which displays the accumulatively stored physical information of said each living subject together with the non-physical information stored in said second memory device.

25. A physical-information collecting system according to claim 21, wherein said measuring device measures at least one of a blood pressure and a pulse rate of said each living subject.

26. A physical-information collecting system according to claim 21, wherein said information reading means comprises a card reading device which reads, from an information card as said recording medium, said one piece of non-physical information recorded on said information card.

27. A physical-information collecting system according to claim 21, wherein said selecting means comprises means for selecting, from said recording medium, said one piece of non-physical information which is independent of said physical information of said each living subject accumulatively stored in said first memory device.

* * * * *